United States Patent [19]

Behner et al.

[11] 3,993,766

[45] Nov. 23, 1976

[54] SUBSTITUTED 2-AMINO-Δ²-THIAZOLINE DERIVATIVES AS ACARICIDAL AGENTS

[75] Inventors: Otto Behner; Wilhelm Stendel, both of Wuppertal, Germany

[73] Assignee: Bayer Aktiengesellschaft, Germany

[22] Filed: Mar. 28, 1975

[21] Appl. No.: 562,833

Related U.S. Application Data

[60] Division of Ser. No. 370,588, June 18, 1973, abandoned, which is a continuation-in-part of Ser. No. 127,405, March 23, 1971, abandoned.

[30] Foreign Application Priority Data

Apr. 2, 1970 Germany............................ 2015675

[52] U.S. Cl. ................................................ 424/270
[51] Int. Cl.² ...................... A01N 9/12; A01N 9/22
[58] Field of Search .............. 424/270; 260/306.7 T

[56] References Cited
UNITED STATES PATENTS

| | | | |
|---|---|---|---|
| 2,027,030 | 1/1936 | Engelmann ............................ | 260/44 |
| 2,261,042 | 10/1941 | Williams ............................. | 260/788 |
| 2,331,995 | 10/1943 | Mathes .............................. | 260/302 |
| 2,345,208 | 3/1944 | Mathes .............................. | 260/302 |
| 2,407,565 | 9/1946 | Mathes .............................. | 260/302 |
| 3,164,605 | 1/1965 | Sovish .............................. | 260/306.7 |
| 3,279,983 | 10/1966 | Baker et al. ........................ | 424/219 |
| 3,600,474 | 8/1971 | Bohner et al. ....................... | 260/957 |
| 3,651,053 | 3/1972 | Sagner et al. ....................... | 260/243 R |

FOREIGN PATENTS OR APPLICATIONS 1,356,908  2/1964  France

OTHER PUBLICATIONS

Najer et al., Bull. Soc. Chim., France, 1960, pp. 960–963.
Tijler, Chem. Abst., vol. 53 (1958) pp. 6208–6209.

*Primary Examiner*—Albert T. Meyers
*Assistant Examiner*—Allen J. Robinson

[57] ABSTRACT

Acaricidal agents and compositions utilizing a 2-amino-Δ²-thiazoline in which the amino group bears an ortho substituted phenyl group, naphth-1-yl, 5,6,7,8-tetrahydronaphth-1-yl or 1,3,5-trimethylpyrazol-4-yl, and salts thereof.

16 Claims, No Drawings

SUBSTITUTED 2-AMINO-Δ²-THIAZOLINE DERIVATIVES AS ACARICIDAL AGENTS

CROSS REFERENCE

This is a divisional of Ser. No. 370,588 filed June 18, 1973, now abandoned, which is in turn a continuation-in-part of Ser. No. 127,405, filed Mar. 23, 1971, now abandoned.

DETAILED DESCRIPTION

This invention pertains to acaricidal 2-substituted-Δ²-thiazolines.

A first aspect of the present invention pertains to (A) compounds of the formula:

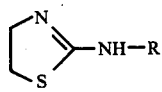  (1)

in which R is (i) phenyl substituted in the 2-position by chloro, bromo, trifluoromethyl or methoxy and further unsubstituted or substituted in either the 4- or 6-position by methyl or methoxy, (ii) 5,6,7,8-tetrahydronaphth-1-yl or (iii) 1,3,5-trimethylpyrazol-4-yl, and (B) addition salts of said Δ²-thiazoline with organic and inorganic acids.

A second aspect of the present invention pertains to acaricidal compositions for use in animals comprising an externally applicable homogeneous mixture of from 0.5 to 90% of a compound selected from the group consisting of (A) a Δ²-thiazoline of the formula:

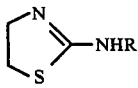  (2)

in which R is (i) phenyl substituted in the 2-position by chloro, bromo, trifluoromethyl, methyl or methoxy and further unsubstituted or substituted in one or both of the 4- and 6-position by methyl, methoxy, chloro or bromo, (ii) 5,6,7,8-tetrahydronaphth-1-yl, (iii) naphth-1-yl or (iv) 1,3,5-trimethylpyrazol-4-yl, and (B) addition salts of said Δ²-thiazoline with organic or inorganic acids, and (II) a liquid or solid carrier, said liquid carrier comprising a surface active agent and at least one member selected from the group consisting of an organic solvent for said Δ²-thiazoline and water and said solid carrier being selected from the group consisting of ground natural minerals and ground synthetic minerals.

A third aspect of the present invention pertains to a method of combatting ectoparasitic acarid which comprises bringing into contact with the acarid an acaricidal amount of a compound selected from the group consisting of (A) a Δ²-thiazoline of the formula:

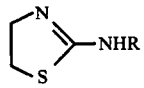

in which R is (i) phenyl substituted in the 2-position by chloro, bromo, trifluoromethyl, methyl or methoxy and further unsubstituted or substituted in one or both of the 4- and 6-position by methyl, methoxy, chloro or bromo, (ii) 5,6,7,8tetrahydronaphth-1-yl, (iii) naphth-1-yl or (iv) 1,3,5-trimethylpyrazol-4-yl, and (B) addition salts of said Δ²-thiazoline with organic or inorganic acids.

Both the free bases of the foregoing Δ²-thiazolines and their salts show strong acaricidal properties, especially against those acarids which, acting as animal ectoparasites, attack, domesticated animals, such as cattle and sheep. The compounds are therefore well suited to combatting animal ectoparasites of the order of the acarids. Ectoparasites of this order which are economically important, especially in tropical and subtropical countries, include the Australian and South American cattle tick, *Boophilus microplus*, the South African cattle tick, *Boophilus decoloratus*, and the multi-host cattle tick and sheep tick, *Hyalomma truncatum*, all from the family of the Ixodoidae.

Over the course of time, ticks have, in various areas, become resistant to the phosphoric acid esters and carbamates hitherto used for combatting them, so that in many areas the success in combatting them has become doubtful. To ensure economical raising of animals in the areas where attack occurs, agents are therefore needed by means of which ticks, including resistant strains, for example the genus Boophilus, can be reliably combatted. In Australia, for example, the Ridgeland strain and the Biarra strain of *Boophilus microplus* have become highly resistant to phosphoric acid esters and carbamates. The present compounds prove equally effective against normally sensitive strains and against resistant strains, for example of Boophilus. They exert a strong egg deposition-inhibiting effect on the adult forms. They are advantageously stable in solution as for example in a cattle dip.

Typical compounds include 2-(2-methyl-phenylamino)-Δ²-thiazoline, 2-(2-methoxy-phenylamino)-Δ²-thiazoline, 2-(2-trifluoromethyl-phenylamino)-Δ²-thiazoline, 2-(2-fluorophenylamino)-Δ²-thiazoline, 2-(2) -chlorophenylamino)-Δ²-thiazoline, 2-(2-bromophenylamino)-Δ²-thiazoline, 2-(2,6-dimethylphenylamino)-Δ²-thiazoline, 2-(2,4-dimethylphenylamino)-Δ²-thiazoline, 2-(2-methyoxy-6-methyl-phenylamino)-Δ²-thiazoline, 2-(2-chloro-6-methyl-phenylamino)-Δ²-thiazoline, 2-(2-chloro-6-methoxy-phenylamino)-Δ²-thiazoline, 2-(2,6-dimethoxy-phenylamino)-Δ²-thiazoline, 2-(2-chloro-6-trifluoromethylphenylamino)-Δ²-thiazoline, 2-(2-methyl-6-trifluoromethylphenylamino)-Δ²-thiazoline, 2-(2-methoxy-6-trifluoromethylphenylamino)-Δ²-thiazoline, 2-(2,6-dichlorophenylamino)-Δ²-thiazoline, 2-(2-methyl-4-chlorophenylamino)-Δ²-thiazoline, 2-naphth-1-ylamino)-Δ²-thiazoline, 2-(5,6,7,8-tetrahydronaphth-1-ylamino)-Δ²-thiazoline, 2-(1,3,5-trimethylpyrazol-4-ylamino)-Δ²-thiazoline and 2-(2,6-dibromo-4-methyl-phenylamino)-Δ²-thiazoline.

Some of the compounds mentioned have already been described as sedatives (see French Patent Specification 1,356,908; H. Najer and R. Guidicelli, Bull. soc. chim. France 1960, 960; and M. Tisler, Arch. Pharm. 291, 457 (1958)). Nothing has been described regarding the action of these ortho-substituted substances against ectoparasites.

The 2-amino-Δ²-thiazolines used in accordance with the invention are obtainable through cyclisation of thioureas of the formula

  (4)

in which

R is as defined above, under the influence of strong acids such as, for example, hydrochloric acid. The intermediates of formula (4) can be prepared by reaction of isothiocyanates of the formula R—NCS or dithiocarbamic acid chlorides of the formula R—NH—C-S—Cl with 2-aminoethanol.

Instead of the thioureas of formula (4), those of the formula

X—CH$_2$—CH$_2$—NH—CS—NH—R  (5)

in which

X represents halogeno or a sulphonic acid group such as, for example, the p-toluenesulphonyloxy radical, can also be used.

In this case, the cyclisation takes place spontaneously without the addition of an acid. This type of reaction can be supported by heating.

The intermediates of the formula (5) are, for example, obtained by reaction of the above isothiocyanates or thiocarbamic acid chlorides with amines of the formula X—CH$_2$—CH$_2$—NH$_2$ or by reaction of isothiocyanates of the formula X—CH$_2$—CH$_2$—NCS with amines of the formula R—NH$_2$.

The 2-amino-Δ$^2$-thiazolines of the invention possess basic properties and thus form salts with inorganic and organic acids, for example hydrochlorides, sulfates, phosphates, nitrates, fumarates, succinates, naphthalenedisulphonates and methanesulphonates.

The method of the present invention is practiced by bringing a compound of formula (3) into contact with an acarid. This can be accomplished either through treatment of an infested animal or prophylactically to animal to prevent infestation.

The compounds are applied by powdering, spraying, watering, atomizing, bathing or dipping.

For this purpose, the compounds are preferably converted into acaricidal formulations, such as solutions, emulsions, suspensions, powders, pastes and granulates. These are produced, for example, by mixing the Δ$^2$-thiazolines with extenders, that is, liquid or solid carriers. The liquid carriers include a surface active agent, that is, emulsifying agents and/or dispersing agents and water, or an organic solvent, as well as mixtures thereof. Solid carriers include ground natural and synthetic minerals.

Examples of emulsifying agents to be used when water is the carrier include nonionic and anionic emulsifiers, such as polyoxyethylene-fatty acid esters, polyoxyethylene-fatty alcohol ethers, as for example alkylarylpolyglycol ethers, alkyl sulfonates and aryl sulfonates. Examples of dispersing agents include lignin, sulfite waste liquors and methyl cellulose.

The liquid diluents or carrier are preferably aromatic hydrocarbons such as xylenes or benzene, chlorinated aromatic hydrocarbons such as chlorobenzenes, liquid paraffins such as mineral oil fractions, alcohols such as methanol or butanol, or strongly polar solvents such as dimethylformamide or dimethylsulfoxide.

As solid diluents or carriers, there are preferably used ground natural minerals, such as kaolins, clays, talc or chalk, or ground synthetic minerals, such as highly-dispersed silicic acid or silicates.

Generally, the formulations contain 0.1 to 95%, preferably 0.5 to 90%, by weight, of at least one Δ$^2$-thiazoline.

Further auxiliary substances and active substances, such as insecticides or disinfectants, can also be mixed in the formulations or the ready-to-use solutions.

The method and compositions of the present invention can be illustrated as follows:

Three parts of the indicated Δ$^2$-thiazoline are mixed with seven parts of a mixture of equal parts by weight of ethylene glycol monomethyl ether and nonylphenol polyglycol ether. The emulsion concentrate thus obtained is diluted with water to the particular use concentration required.

Adult, gorged female ticks of the variety *Boophilus microplus* (resistant) are dipped for one minute into this active substance preparation. After dipping groups of 10 female specimens of the various strains of ticks, the individual ticks are transferred to plastic dishes, the bottom of which is covered with a disc of filter paper. After 35 days, the effectiveness of the preparation is assessed by determining the inhibition of the deposition of fertile eggs as compared to the egg deposition of untreated control ticks. The action is indicated in %, with 100% denoting that no fertile eggs were deposited, and 0% denoting that the ticks have deposited eggs in the normal manner, corresponding to the untreated control ticks.

The compounds tested, concentration, parasites tested and findings obtained are shown in the following table:

Table

| *In vitro* test of the egg deposition-inhibiting action on ticks (*Boophilus microplus*, Biarra strain) | | |
|---|---|---|
| | % Concentration Giving Indicated Inhibition | |
| Active Substance | 100% | 50% |
| 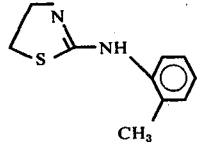 | 1.0 | 0.8 |
| 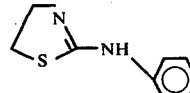 | 1.0 | 0.3 |
|  | 0.1 | 0.05 |
| 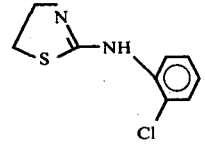 | 1 | 0.8 |
| 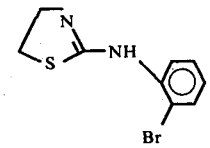 | 0.1 | 0.03 |
| 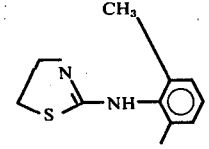 | 0.3 | 0.08 |
| 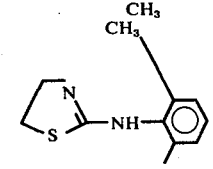 | | |

Table-continued

*In vitro* test of the egg deposition-inhibiting action on ticks (*Boophilus microplus*, Biarra strain)

| Active Substance | % Concentration Giving Indicated Inhibition 100% | 50% |
|---|---|---|
| [thiazoline-NH-phenyl with Cl, CH₃ substituents] | 0.1 | 0.03 |
| [thiazoline-NH-phenyl with CH₃O, CH₃O substituents] | 0.1 | 0.03 |
| [thiazoline-NH-phenyl with CH₃O, Cl substituents] | 0.03 | 0.02 |
| [thiazoline-NH-biphenyl] | 0.2 | 0.08 |
| [thiazoline-NH-naphthyl (H)] | 0.3 | 0.2 |
| [thiazoline-NH-pyrazole with CH₃, CH₃, CH₃ substituents] | 0.1 | 0.08 |
| [thiazoline-NH-phenyl with CH₃, CH₃ substituents] | 0.1 | 0.03 |
| [thiazoline-NH-phenyl with CH₃, Cl substituents] | 0.1 | 0.05 |

The following examples will serve to further typify the nature of the present invention without being a limitation on the scope thereof.

EXAMPLE 1

2-(2-Chlorophenylamino)-$\Delta^2$-thiazoline 16.9 g (0.1 mol) of 2-chlorophenylisothiocyanate are added to a solution of 6.1 g (0.1 mol) of 2-aminoethanol in 50 ml of methylene chloride, over the course of 30 minutes, while stirring. The mixture is stirred for a further hour under reflux and is then evaporated to dryness under reduced pressure; the residue is treated with 50 ml of concentrated hydrochloric acid, and the reaction mixture is stirred for one hour under reflux. The batch is then evaporated to dryness and the residue (hydrochloride) is recrystallized from an ethanol/ether mixture. The product melts at 178° – 180° C. The yield is 22.6 g (91% of theory).

The following compounds can be prepared by processes analogous to that given above.

2-(2-Methylphenylamino)-$\Delta^2$-thiazoline, base, melting point: 105° – 106° C.

2-(2-Trifluoromethylphenylamino)-$\Delta^2$-thiazoline, base, melting point: 140° – 141° C.

2-(2-Bromophenylamino)-$\Delta^2$-thiazoline, base, melting point: 158° – 159° C.

2-(2,6-Dimethylphenylamino)-$\Delta^2$-thiazoline, base, melting point: 107° – 108° C.

2-(2-Methoxy-6-methylphenylamino)-$\Delta^2$-thiazoline, base, melting point: 126° – 127° C.

2-(2-Chloro-6-methylphenylamino)-$\Delta^2$-thiazoline, base, melting point: 140° – 143° C.

2-(2,6-Dimethoxyphenylamino)-$\Delta^2$-thiazoline, base, melting point: 156° – 158° C.

2-Naphth-1-ylamino-$\Delta^2$-thiazoline, base, melting point: 154° – 161° C.

2-(5,6,7,8-Tetrahydronaphth-1-ylamino)-$\Delta^2$-thiazoline, base, melting point: 120° – 124° C.

2-(1,3,5-Trimethylpyrazol-4-ylamino)-$\Delta^2$-thiazoline, base, melting point: 151° – 153.5° C.

EXAMPLE 2

2-(2,6-Dichlorophenylamino)-$\Delta^2$-thiazoline

A solution of 24.3 g (0.15 mol) of 2,6-dichloroaniline and 25.8 g (150 mol %) of thiophosgene in 150 ml of dry ethylene chloride is stirred overnight under reflux and then evaporated to dryness under reduced pressure; and crude 2,6-dichlorophenyl-thiocarbamic acid chloride is taken up in 100 ml of absolute benzene, and the impurities are filtered off and rinsed with absolute benzene. The filtrate is slowly added dropwise, at room temperature, to a solution of 20 g (0.33 mol) of 2-aminoethanol in 100 ml of absolute benzene, and the mixture is stirred for a further four hours under reflux and again evaporated to dryness under reduced pressure. The residue, consisting of N-(2,6-dichlorophenyl)-N'-2-hydroxyethyl-thiourea and 2-aminoethanol hydrochloride, is stirred with 90 ml of concentrated hydrochloric acid for one hour, under reflux. After cooling, the batch is diluted with 200 ml of water and rendered alkaline with concentrated sodium hydroxide solution with cooling, and the precipitate is recrystallized from a benzene/ligroin mixture. The product melts at 174° – 176° C. The yield is 25.6 g (69% of theory).

2-(2,6-Dibromo-4-methylphenylamino)-$\Delta^2$-thiazoline, melting point 191° – 193° C, can be prepared analogously.

EXAMPLE 3

12.1 g (0.1 mol) of 2-chloroethylisothiocyanate are added to a solution of 12.1 g (0.1 mol) of 2,6-xylidine in 100 ml of absolute toluene over the course of 45 minutes, while cooling in ice. The mixture is stirred for one hour at room temperature and subsequently for five hours under reflux. After cooling, the supernatant solution is decanted, the residue is taken up in water and then rendered alkaline with sodium hydroxide solution, and the crude base is filtered off and recrystallized from ligroin. It melts at 107° – 108° C. The yield is 18.0 g (87% of theory).

EXAMPLE 4

The following compounds may be prepared in a manner analogous to that described in Example 1:

2-(2-ethoxynaphth-1-ylamino)-Δ²-thiazoline, hydrochloride melting point: 187° – 189° C; 2-(2,4-dimethylphenylamino)-Δ²-thiazoline, melting point: 84° C; and 2-(2-methyl-4-chlorophenylamino)-Δ²-thiazoline, melting point: 138° – 140° C.

What is claimed is:

1. A method of combatting ectoparasitic acarids which comprises contacting said acarids with an acaricidally effective amount of a compound selected from the group consisting of (A) a Δ²-thiazoline of the formula:

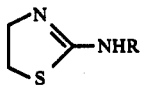

in which R is (i) phenyl substituted in the 2-position by chloro, bromo, trifluoromethyl, methyl or methoxy and further unsubstituted or substituted in one or both of the 4- and 6-position by methyl, methoxy, chloro or bromo, (ii) 5,6,7,8-tetrahydronaphth-1-yl, (iii) naphth-1-yl or (iv) 1,3,5-trimethylpyrazol-4-yl, and (B) addition salts of said Δ²-thiazoline with organic or inorganic acids.

2. The method according to claim 1, wherein said Δ²-thiazoline is 2-(2,4-dimethylphenylamino)-Δ²-thiazoline.

3. The method according to claim 1, wherein said Δ²-thiazoline is 2-(2-methyl-4-chlorophenylamino)-Δ²-thiazoline.

4. The method according to claim 1, wherein said Δ²-thiazoline is 2-(2-chlorophenylamino)-Δ²-thiazoline.

5. The method according to claim 1, wherein said Δ²-thiazoline is 2-(2-methylphenylamino)-Δ²-thiazoline.

6. The method according to claim 1, wherein said Δ²-thiazoline is 2-(2-trifluoromethylphenylamino)-Δ²-thiazoline.

7. The method according to claim 1, wherein said Δ²-thiazoline is 2-(2-bromophenylamino)-Δ²-thiazoline.

8. The method according to claim 1, wherein said Δ²-thiazoline is 2-(2,6-dimethylphenylamino)-Δ²-thiazoline.

9. The method according to claim 1, wherein said Δ²-thiazoline is 2-(2-methoxy-6-methylphenylamino)-Δ²-thiazoline.

10. The method according to claim 1, wherein said Δ²-thiazoline is 2-(2-chloro-6-methylphenylamino)-Δ²-thiazoline.

11. The method according to claim 1, wherein said Δ²-thiazoline is 2-(2,6-dimethoxyphenylamino)-Δ²-thiazoline.

12. The method according to claim 1, wherein said Δ²-thiazoline is 2-naphth-1-ylamino-Δ²-thiazoline.

13. The method according to claim 1, wherein said Δ²-thiazoline is 2-(5,6,7,8-tetrahydro-1-naphthylamino)-Δ²-thiazoline.

14. The method according to claim 1, wherein said Δ²-thiazoline is 2-(1,3,5-trimethylpyrazol-4-ylamino)-Δ²-thiazoline.

15. The method according to claim 1, wherein said Δ²-thiazoline is 2-(2,6-dichlorophenylamino)-Δ²-thiazoline.

16. The method according to claim 1, wherein said Δ²-thiazoline is 2-(2,6-dibromo-4-methylphenylamino)-Δ²-thiazoline.

* * * * *